US005204247A

United States Patent [19]
Adachi et al.

[11] Patent Number: 5,204,247
[45] Date of Patent: Apr. 20, 1993

[54] LACTOBACILLUS SP. KPB-167 AND METHOD OF MANUFACTURING VISCOSE POLYSACCHARIDES EMPLOYING THE SAME

[75] Inventors: Susumu Adachi; Takahiro Toba; Takao Mukai, all of Sendai; Takashi Watanabe, Kamakura; Haruhiko Yokoi, Hiratsuka, all of Japan

[73] Assignee: Sumitomo Heavy Industries, Ltd., Tokyo, Japan

[21] Appl. No.: 785,176

[22] Filed: Oct. 30, 1991

Related U.S. Application Data

[63] Continuation of Ser. No. 376,686, Jul. 7, 1989, abandoned.

[30] Foreign Application Priority Data

Jul. 13, 1988 [JP] Japan .................. 63-175637

[51] Int. Cl.$^5$ ............................. C12P 19/04
[52] U.S. Cl. .................. 435/101; 435/252.9; 435/853; 435/854; 435/855; 435/856; 435/857; 435/885; 536/114
[58] Field of Search ............. 435/101, 252.9, 853–857, 435/885; 536/114

[56] References Cited

U.S. PATENT DOCUMENTS

| | | | |
|---|---|---|---|
| 2,770,573 | 11/1956 | György et al. | 435/853 |
| 3,830,697 | 8/1974 | Yoshida et al. | 435/853 |
| 4,444,793 | 4/1984 | Schwartz et al. | 435/101 |
| 4,514,424 | 4/1985 | Raccach | 435/853 |
| 4,588,595 | 5/1986 | Okonogi et al. | 435/885 |

OTHER PUBLICATIONS

Chemical Abstracts, vol. 68, No. 3, Jan. 15, 1968, pp. 981–982, Abstract No. 10385x, J. W. M. LaRiviere et al., "Kefiran, a Novel Polysaccharide Produced in the Kefir Grain by Lactobacillus Brevis", and Arch. Mikrobiol. 59(1–3), 269–78 (1967) *Abstract*.

Milchwissenschaft, vol. 42, No. 9, 1987, pp. 565–568, Toba et al., "Comparative Study of Polysaccharides from Kefir Grains, an Encapsuled Homofermentative Lactobillus Species and Lactobacillus Kefir", *p. 567*.

Agricultural and Biological Chemistry, vol. 50, No. 10, 1986, pp. 2673–2674, Toba et al., "A Medium for the Isolation of Capsular Bacteria from Kefir Grains", *Whole Article*.

Chemical Abstracts, vol. 69, No. 12, Sep. 16, 1968, p. 4146, Abstract No. 44135b, Kooiman, "Chemical Structure of Kefiran, the Water-Soluble Polysaccharides of the Kefir Grain", and Carbohyd. Res. 1968, 7(2), 200–11 *Abstract*.

Yokoi et al., *J. Dairy Sci.*, vol. 73(7), 1990, pp. 1684–1689.

Yokoi et al., *Int. J. of Food Microb.*, vol. 13, 1991, pp. 1–9.

Toba et al., *Bioscience and Industry*, vol. 47(4),, 1989, pp. 43–45.

*Primary Examiner*—Johnnie R. Brown
*Assistant Examiner*—Pamela S. Webber
*Attorney, Agent, or Firm*—Flynn, Thiel, Boutell & Tanis

[57] ABSTRACT

A new strain Lactobacillus sp. KPB-176, which does not possess strict selectivity for specific media and which involves no reduction in the productivity of polysaccharides even during subculture, was isolated from kefir grains. When this new strain is cultured on a medium containing milk whey and casamino acid or when on a medium containing carbohydrate and yeast extract, capsular polysaccharides are produced in high yields.

5 Claims, 1 Drawing Sheet

LACTOBACILLUS SP. KPB-167 AND METHOD OF MANUFACTURING VISCOSE POLYSACCHARIDES EMPLOYING THE SAME

This application is a continuation of U.S. Ser. No. 07/376,686, filed Jul. 7, 1989, now abandoned.

BACKGROUND OF THE INVENTION

The present invention relates to a new strain Lactobacillus sp. KPB-167 (the Accession Number given to this by the International Depositary Authority is FERM BP-2303) that belongs to the genus Lactobacillus and is isolated from kefir grains. The present invention also relates to a method of manufacturing viscose polysachharides in which this new strain is cultured on a predetermined medium.

Kefir grains are known as the starter of kefir, a type of fermented milk traditionally known in the Caucasus, U.S.S.R. Kefir grains are lumps of microorganisms such as lactic acid bacteria and yeasts in symbiosis wherein the support medium is provided by polysaccharides produced by capsule forming bacteria. Since polysaccharides produced by capsule forming bacteria are capable of exhibiting such favorable actions as the promotion of digestive functions, and antitumor actions, they are used as medicines. They are also used in a wide variety of applications such as food additives employed to cause thickening or gelation of a food, and functional macromolecular materials.

Capsule forming bacteria were previously isolated from kefir grains by Rossi et. al. (1978), Ohara (1980), Ohta et. al. (1984), and Adachi et. al. (1986). However, all of the previously isolated strains have strong selectivity for specific media. For instance, according to the method disclosed in Japanese Patent Laid-Open No. 257197/1986 which employs the strain Lactobacillus WT-1 previously isolated by Adachi et. al., a medium containing wine as the essential component must be used, and it is impossible to manufacture polysaccharides otherwise. Furthermore, the conventionally isolated strains have involved the drawback that the productivity of polysaccharides drops during subculture (or preservation).

SUMMARY OF THE INVENTION

The present inventors have conducted various studies in the pursuit of a new strain which does not possess strict selectivity for specific media for the production of polysaccharides, and which involves no reduction in the productivity of polysaccharides even during subculture. As a result, the present inventors have found that a new strain Lactobacillus sp. KPB-176, which was isolated from kefir grains, is such a strain. They have also found that, if this new strain is cultured on a medium, in particular, a medium containing milk whey and casamino acid or a medium containing carbohydrate and yeast extract, capsular polysaccharides are produced in high yields.

DETAILED DESCRIPTION OF THE INVENTION

Figure 1:
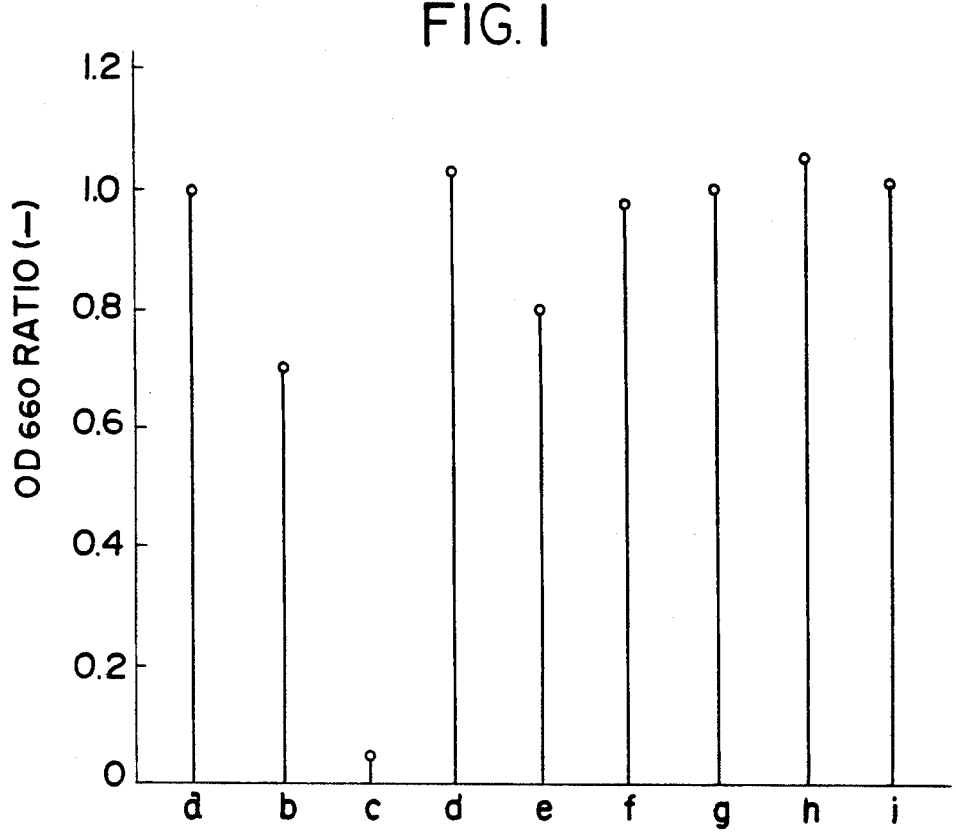
FIGS. 1 and 2 show the relationship between the proliferation of the new strain Lactobacillus sp. KPB-167 of the present invention and various media.

The new strain Lactobacillus sp. KPB-167 (FERM BP-2303) is a kind of long-rod bacilli which belongs to the genus Lactobacillus and which is isolated from kefir grains. The strain of the present invention has the following bacteriological characteristics.

A Strain Morphology (1) Cell Size: 1 to $1.5 \times 15$ to 60 ($\mu$m)
(2) Shape: rod-shaped
(3) Motility: nil
(4) Spore Formation: nil
(5) Gram Stain: positive

B State of Growth on Medium

Bacteria were measured on a milk whey agar medium having the following composition, and anaerobic culture (by a gas-pak method or a gloved-box method) was conducted at 30° C. for one week. The resultant colony was observed.

| (Medium Composition) | |
|---|---|
| milk whey* | 100 ml |
| lactose | 1 g |
| casamino acid | 0.5 g |
| L-cysteine hydrochloride | 0.05 g |
| sodium acetate | 0.5 g |
| tween 80** | 0.1 g |
| minerals B*** | 1 ml |
| agar | 2 g |
| pH | 5.5 |

*A filtrate obtained by boiling for 30 minutes a 10%-solution of skimmed milk whose pH value was adjusted to 4.6 by lactic acid, and filtering the boiled solution to remove the deposit.
**Trade name for polyoxyethylene sorbitan monooleate
***Composition:

| | |
|---|---|
| $MgSO_4.7H_2O$ | 4 g |
| $MnSO_4.4H_2O$ | 0.15 g |
| $FeSO_4.7H_2O$ | 0.18 g |
| NaCl | 0.1 g |
| distilled water | 100 ml |

Colony Observation Results

Shape: circular
Size: 2 to 4 mm
Elevation: convex circular
Peripheral Edge: Smooth
Surface: smooth
Color: white
Transparency: translucent
Hardness: viscose
Structure: uniform and drop-like

C Physiological Characteristics

1 Growth Temperature:
  30° C. (optimum)
  20° to 35° C. (growable range)
2 Growth pH:
  5.5 to 6 (optimum),
  5 to 7.5 (growable range)
3 Attitude to Oxygen: The strain does not require aeration and is anaerobic. Although it grows by aerobic culture, it grows better in a $CO_2$ atmosphere.
4 Chromogenesis: nil
5 Catalase: negative 6 Optical Rotation Power of Lactic Acid Produced from Carbohydrate: D(L) type
7 Production of Acid and Gas from carbohydrates:

|      |                | Acid Production | gas Production |
|------|----------------|-----------------|----------------|
| (1)  | D(−)-Arabinose | −               | −              |
| (2)  | D(+)-xylose    | −               | −              |
| (3)  | α-L-rhamnose   | −               | −              |
| (4)  | D-ribose       | −               | −              |
| (5)  | glucose        | +               | −              |
| (6)  | D-mannose      | +               | −              |
| (7)  | D(−)-fructose  | +               | −              |
| (8)  | D-galactose    | +               | −              |
| (9)  | sucrose        | +               | −              |
| (10) | maltose        | +               | −              |
| (11) | cellobiose     | −               | −              |
| (12) | lactose        | +               | −              |
| (13) | trehalose      | −               | −              |
| (14) | melibiose      | −               | −              |
| (15) | raffinose      | −               | −              |
| (16) | melezitose     | −               | −              |
| (17) | D-mannitol     | −               | −              |
| (18) | D-sorbitol     | −               | −              |
| (19) | esculin        | −               | −              |
| (20) | salicin        | −               | −              |
| (21) | amygdalin      | −               | −              |

When the above-stated bacteriological characteristics of the strain were compared with various descriptions given by "Bergey's Manual of Systematic Bacteriology Vol. 2" and "Cho-nai Kin no Sekai (the World of Inne-intestinal Bacteria)" by Tomotari Mitsuoka, it was found that the strain belonged to the genus Lactobacillus. Therefore, the strain was classified as "Lactobacillus sp. KPB-167". This strain was originally deposited at the culture depository, Fermentation Research Institute, Agency of Industrial Science and Technology, located at 1-3, Higashi 1-chome, Tsukuba-shi, Ibaragi-ken, Japan, under the accession number P-9886 on Feb. 24, 1988.

As mentioned before, several strains of capsule forming bacteria, which are a kind of homofermentative lactic acid bacteria of the genus Lactobacillus, have previously been isolated from kefir grains. The results of comparing physiological characteristics of these known strains with the strain of the present invention are shown in Table 1.

TABLE 1

Physiological Comparison between Capsule Forming Bacteria Isolated from Kefir Grains

| Isolator & Lactobacillus sp. No. | KPB-167 | Adachi et al.[1), 2)] WT1 | WT2B etc. | Ohara[3)] S-10-LR | Ohta et al[4)] A3-1 etc. | Rossi et al[5)] FIM−F20M |
|---|---|---|---|---|---|---|
| Bacteria Size (μ) | 1~1.5 × 15~60 | 0.4~1 × 3.5~20 | 0.8~1.2 × 3.0~20 | 1.2 × 2.0~10 | 0.8~1 × 3~10 | − |
| Growth Temp. (°C.) | 20~35 | 20~30 | 20~30 |  |  |  |
| (Optimum Temp.) (°C.) | (30) | (30) | (30) | (30) | (30) | (30) |
| Growth pH | 5~7.5 | 5~6 | 5~6 |  | 5.0~6.5 |  |
| (Optimum pH) | (5.5~6) | (5.5) | (5.5) | − | (5.5) | − |
| Note 1) Fermentation saccharide |  |  |  |  |  |  |
| Arabinose | − | − | − | − | − | − |
| xylose | − | − | − | − | − | − |
| rhamnose | − | − | − | − | − | − |
| ribose | − | − | − | − | − |  |
| glucose | + | + | + | + | + | + |
| mannose | + | + | − | − | + |  |
| fructose | + | + | + |  | + |  |
| galactose | + | + | + | + | + | + |
| sucrose | + | + | + | + | + | + |
| maltose | + | + | + | + | + | + |
| cellobiose | − | − | − | − | − | − |
| lactose | + | + | + | + | + | + |
| trehalose | − |  | − | − | .− | − |
| melibiose | − |  | + | − | + | + |
| raffinose | − |  | + | + | + | − |
| melezitose | − | − | − |  | − | − |
| mannitol | − | − | − | − | − | − |
| sorbitol | − | − | − | − | − | − |
| esculin | − | − | − | − |  |  |
| salicin | − | − | − |  | − | − |
| amygdalin | − |  | − |  | − | − |
| Note 2) Lactic Acid Produced | D(L) | D | D(L) | D | D(L) | ? |

Note 1)
+: positive (the carbohydrate is usable);
−: negative (the carbohydrate is not usable)

Note 2)
D = 0~20%;
D(L) = 20~40%;
DL = 40~60%
(L-lactic acid ratio in % to the total lactic acid)

Literature Cited
[1)] Adachi et. al.: Japanese Patent Laid-Open Nos. 247378/1986 & 257197/1986
[2)] T. Fujisawa, et. al.: INTERNATIONAL JOURNAL OF SYSTEMATIC BACTERIOLOGY, N-14, JAN. 1988
[3)] Naohiro Ohara: Thesis for Degree, Tokyo Nogyo Daigaku, (1980)
[4)] Toshiko Ohta et. al.: Sagami Jyoshidaigaku Kiyo, 47, 19 (1984)
[5)] J. Rossi: SCINZA E TELNICA LATTIERO-CAZEARID, 29, 2, 1978

According to the present invention, capsular polysaccharides are manufactured by culturing the strain Lactobacillus sp. KPB-167 on a suitable medium, and isolating capsular polysaccharides from the resultant culture solution then refining the isolated polysaccharides. Although it is possible to culture the strain Lactobacillus sp. KPB-167 on a medium suitably containing a carbon source, a nitrogen source, salts, and vitamins, in a similar manner to the case of the culture of an ordinary microorganism, it is important to select a suitable medium in order to obtain capsular polysaccharides in high yields.

For the purpose of examining the nutrient requirement of the strain of the present invention, the following experiments 1 and 2 were conducted using media A and B, respectively. The media A and B had the compositions shown in Table 2.

TABLE 2

| Compositions of Media | Media A | Media B |
| --- | --- | --- |
| milk whey* | 100 ml | — |
| lactose | 1 g | 10 g |
| casamino acid | 0.5 g | — |
| L-cysteine hydrochloride | 0.05 g | — |
| sodium acetate | 0.5 g | 0.5 g |
| tween 80 | 0.1 g | 0.1 g |
| minerals B | 1 ml | — |
| tryptone | — | 1 g |
| meat extract | — | 1 g |
| yeast extract | — | 0.5 g |
| dipotassium hydrogenphosphate | — | 0.2 g |
| diammonium citrate | — | 0.2 g |
| magnesium sulfate | — | 0.06 g |
| manganese sulfate | — | 0.03 g |
| distilled water | — | 100 ml |
| pH | 5.5 | 5.5 |
| agar | 2 g | 2 g |

*In case of a liquid medium, the above-listed milk whey is a filtrate obtained by boiling for 30 minutes a 10%-solution of skimmed milk after its pH value has been adjusted to 4.6 by hydrochloric acid, filtering the boiled solution to obtain a primary filtrate, boiling this filtrate for 30 minutes after its pH value has been adjusted to 6.8 by NaOH, and further filtering the boiled filtrate.

In case of an agar medium, the above-listed milk whey is a filtrate obtained by boiling for 30 minutes a 10%-solution of skimmed milk after its pH value has been adjusted to 4.6 by lactic acid, and filtering the boiled solution.

Examination 1

A medium (a) having exactly the same composition as the medium A and various other media (b) to (i), listed below, were prepared. Each of the media (b) to (i) had the same composition as the medium A shown in Table 2 except that one particular component was omitted. For instance, the medium indicated as "medium A - milk whey" in the following list had the same composition as the medium A except that it contained no milk whey. These media were individually placed in screw-capped tubes, and sterilized for 15 minutes at 120° C. Subsequently, the strain Lactobacillus sp. KPB-167 was inoculated into each medium within the tube, and, after $CO_2$ substitution, shake culture was conducted for three days at 30° C. Thereafter, the $OD_{660}$ of each of the resultant culture solutions was measured by means of an absorbancy photometer to examine the proliferation of the strain. The results of this measurement are shown in FIG. 1.

(a): medium A
(b) milk whey alone
(c): medium A—milk whey
(d): medium A—lactose
(e): medium A—casamino acid
(f): medium A—L-cysteine hydrochloride
(g): medium A—minerals B
(h): medium A—sodium acetate
(i): medium A—tween 80

FIG. 1 shows the $OD_{660}$ values of the culture solutions obtained using the media (b) to (i), each shown as a value relative to the $OD_{660}$ value of the culture solution obtained using the medium A. As will be seen from this figure, the strain failed to grow on the medium (c) whose component was the same as the medium A except that it contained no milk whey. The medium (e) which contained no casamino acid permitted only a small proliferation amount. It is conjectured, from these facts found in the examination, that the strain has strong nutrient requirement for milk whey, and that casamino acid has the effect of promoting the proliferation of the strain.

Examination 2

A medium (a) having exactly the same composition as the medium B and various other media (b) to (k), listed below, were prepared. Each of the media (b) to (k) had the same composition as the medium B shown in Table 2 except that one particular component was omitted. The strain Lactobacillus sp. KPB-167 was proliferated by the same method and under the same conditions as those used in Examination 1. The results are shown in FIG. 2.

Figure 2:
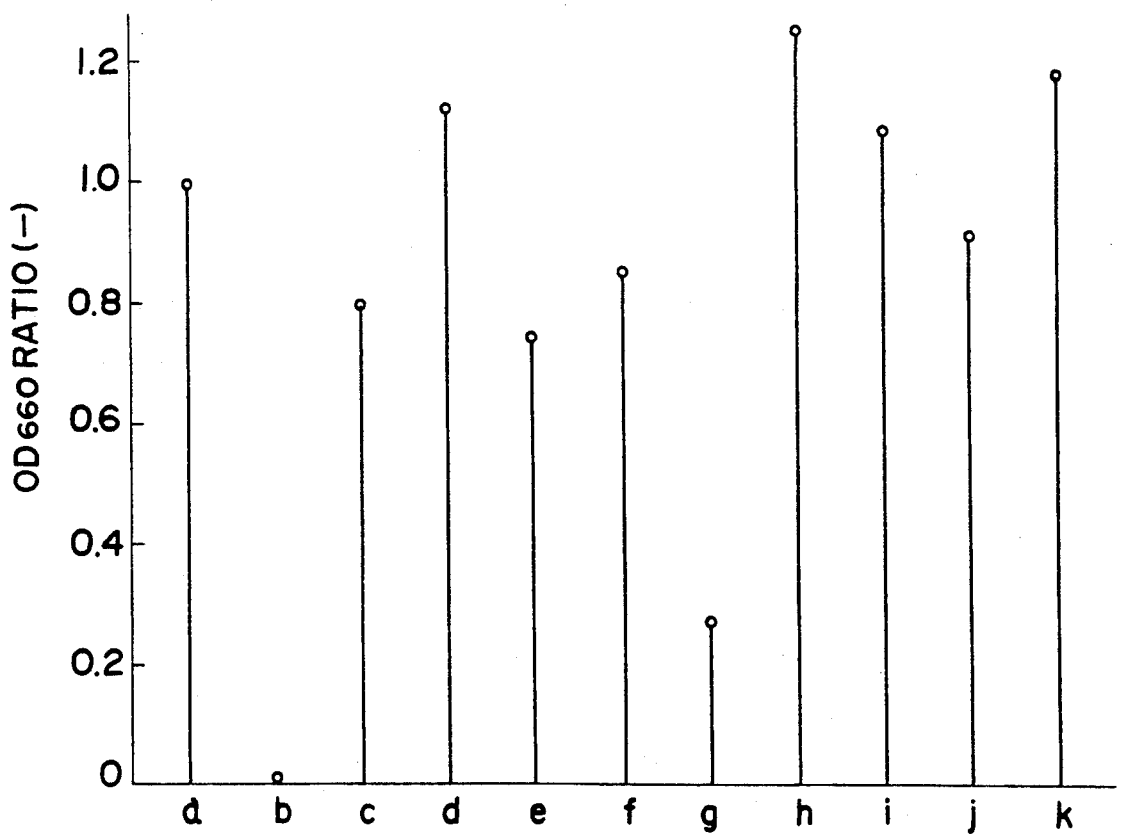

(a): medium B
(b): medium B—lactose
(c): medium B—sodium acetate
(d): medium B—tween 80
(e): medium B—tryptone
(f): medium B—meat extract
(g): medium B—yeast extract
(h): medium B—disodium hydrogenphosphate
(i): medium B—disodium citrate
(j) medium B—magnesium sulfate
(k) medium B—manganese sulfate FIG. 2 shows the $OD_{660}$ values of the culture solutions obtained using the media (b) to (k), each shown as a value relative to the $OD_{660}$ value of the culture solution obtained using the medium B. As will be seen from this figure, in such media containing no milk whey, a carbohydrate (lactose) is of course necessary. Besides this, the strain has relatively strong nutrient requirement for yeast extract. Furthermore, sodium acetate, tryptone, and meat extract each show the effect of promoting the proliferation of the strain. In addition, it was confirmed that it is possible to use, as a carbohydrate to be contained in a medium of this type, a disaccharide such as lactose or sucrose, a monosaccharide such as glucose, galactose, fructose, or a combination thereof.

From the above-described results of the examinations, the following can be deduced. In the case of a medium containing milk whey as its main component, such a medium should contain, in addition to milk whey, casamino acid, and the medium may further contain, as its arbitrarily added components, substances listed in Table 2. In the case of a medium containing no milk whey, such a medium should contain, as its main components, a monosaccharide and/or a disaccharide, and also yeast extract, and the medium may further contain, as its arbitrarily added components, substances listed in Table 2. In fact, when the Lactobacillus sp. KPB-167 was cultured on media having the above-specified features, it was found that good growth condition was maintained, and no drop was seen in the productivity of polysaccharides even during subculture (preservation), as will be described later in Examples.

Polysaccharides are recovered from the culture solution resulting from the culture of the strain Lactobacillus sp. KPB-167 of the present invention in the following manner. The culture solution is centrifuged for 30 minutes at, for instance, 10000 rpm, thereby obtaining a first supernatant fluid. Subsequently, the resultant deposit is suspended in a small amount of distilled water, and the suspension is boiled for 30 minutes. Thereafter, the boiled suspension is centrifuged, thereby obtaining a second supernatant fluid. Because polysaccharides produced by the strain Lactobacillus sp. KPB-167 are contained in both the first and second supernatant fluids, these fluids are usually mixed together and cooled, an equivalent amount of ethanol is added, and the resultant deposit is recovered. The deposit recovered is subjected to a process in which the deposit is dissolved in a small amount of distilled water, the solution is cooled, an equivalent amount of cold ethanol is added, and the resultant deposit is recovered. When this process has been repeated several times, refined polysaccharides can be obtained.

Polysaccharides obtained in this manner have the following properties:

General Properties: They are in the form of a white, tasteless and odorless powder, are insoluble in ethanol, methanol, or acetone, are soluble in water, and show high viscosity.

Composite Saccharides: When they were subjected to hydrolysis using an acid (4N-trifluoro-acetic acid) for 3 hours at 100° C., and were then analyzed using a liquid chromatography, the ratio between glucose and galactose was found to be about 1:1.

Molecular Weight: 1 million to 2 million according to a measurement by a gel filtration method (using Asahipak GS-710 columns)

Viscosity: Measurement using a Cannon-Fenske viscometer showed that the absolute viscosity of their 0.1 to 0.5%-aqueous solution was 10 to 70 st.

EXAMPLE 1

2 l of a medium having exactly the same composition as the media A shown in Table 2 was placed in a 2 l-capacity Erlenmeyer flask, and was then subjected to high-pressure sterilization for 15 minutes at 120° C. Thereafter, 40 ml of a culture solution resulting from previous culture of the strain Lactobacillus sp. KPB-167 was added to the medium. After $CO_2$ substitution for 5 minutes, the flask was tightly closed by a silicon cap, and the strain was stationary-cultured for 92 hours at 30° C.

2 l of a culture solution resulting from the culture was centrifuged for 30 minutes at 10000 rpm, thereby obtaining a supernatant fluid (A) and a deposit. The deposit was suspended in 100 ml of distilled water, and the suspension was subjected to heat extraction in a boiling water-bath for 30 minutes, thereby dissolving polysaccharides into the solvent. The resultant suspension was centrifuged for 30 minutes at 10000 rpm, thereby obtaining a supernatant fluid (B). The supernatant fluids (A) and (B) were mixed with an equivalent amount of cold ethanol, and the mixture was maintained stationary in cold water for 15 minutes. Thereafter, the resultant mixture was again centrifuged for 30 minutes at 10000 rpm, thereby recovering polysaccharides as a deposit.

The deposit was dissolved in 50 ml of distilled water, an equivalent amount of cold ethanol was added, and the polysaccharides were again recovered in a similar manner. These operations were repeated three times to refine the polysaccharides. After freeze-dry, a white powder weighing 1.0 g was obtained.

The obtained white powder was subjected to hydrolysis using 4N-trifluoro acetic acid for 3 hours at 100° C., and was then analyzed by means of a liquid chromatography in which Shodex Sugar Pak columns were used. As a result, the white powder was found to be polysaccharides containing glucose and galactose at a composition ratio of about 1:1. When the molecular weight was measured by a gel filtration method using Asahipak GS-710 columns, the molecular weight was found to be 1 million to 2 million.

EXAMPLE 2

3 l of a medium (a modified MRS medium) having exactly the same composition as the media B shown in Table 2 was placed in a 3 l-capacity culturing flask, and was then subjected to high-pressure sterilization for 15 minutes at 120° C. Thereafter, 60 ml of a culture solution resulting from previous culture of the strain Lactobacillus sp. KPB-167 was added to the medium. After $CO_2$ substitution for 5 minutes, the flask was tightly closed, and the strain was spinner-cultured at a low speed for 92 hours at 30° C.

3 l of a culture solution resulting from the culture was processed in the same way as in Example 1, thereby obtaining a powder of polysaccharides that weighed 1.8 g.

The composite saccharides and the molecular weight were examined and measured. The results of the examination and measurement corresponded to those of Example 1.

EXAMPLE 3

A culture operation was conducted using the same conditions as those in Example 2, except that the pH value of the medium was controlled at 5.5 with sodium hydrate during culturation. As a result, polysaccharides weighing 3.5 g, or weighing about two times the product of the Example 2, was obtained.

EXAMPLE 4

Culture operations were conducted using the same conditions as those in Example 3, except that the carbohydrate contained in each of the media was changed from lactose in Example 3 to sucrose, glucose, fructose, galactose, or a mixture thereof. The results achieved were substantially the same as those achieved in Example 3.

We claim:

1. A process of manufacturing Kefiran comprising the steps of: culturing Lactobacillus sp. KPB-167 on a medium containing milk whey and casamino acid; and separating and collecting the Kefiran produced.

2. A process of manufacturing Kefiran comprising the steps of: culturing Lactobacillus sp. KPB-167 on a medium containing a carbohydrate and yeast extract; and separating and collecting the Kefiran produced.

3. A process according to claim 2, wherein said carbohydrate is a member selected from the group consisting of a monosaccharide, a disaccharide and mixtures thereof.

4. A process according to claim 3, wherein said monosaccharide is one selected from the group consisting of glucose, galactose, and fructose, while said disaccharide is one selected from the group consisting of lactose and sucrose.

5. A culture medium containing Lactobacillus sp. KPB-167, milk whey and casamino acid which produces recoverable amounts of Kefiran.

* * * * *